(12) United States Patent
Bedez et al.

(10) Patent No.: US 11,908,174 B2
(45) Date of Patent: Feb. 20, 2024

(54) METHODS AND SYSTEMS FOR IMAGE SELECTION

(71) Applicant: GE Precision Healthcare LLC, Wauwatosa, WI (US)

(72) Inventors: Mathieu Bedez, Bas-Rhin (FR); Marouane Belhaj, Yvelines (FR); Vincent Pangon, Bas-Rhin (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 139 days.

(21) Appl. No.: 17/646,609

(22) Filed: Dec. 30, 2021

(65) Prior Publication Data
US 2023/0230356 A1    Jul. 20, 2023

(51) Int. Cl.
| | |
|---|---|
| *G06V 10/77* | (2022.01) |
| *G16H 30/40* | (2018.01) |
| *G06V 20/70* | (2022.01) |
| *G06V 40/10* | (2022.01) |
| *G06V 10/22* | (2022.01) |
| *G06T 11/00* | (2006.01) |
| *G06V 10/82* | (2022.01) |

(52) U.S. Cl.
CPC .......... *G06V 10/7715* (2022.01); *G06T 11/00* (2013.01); *G06V 10/22* (2022.01); *G06V 10/82* (2022.01); *G06V 20/70* (2022.01); *G06V 40/10* (2022.01); *G16H 30/40* (2018.01); *G06T 2210/21* (2013.01); *G06T 2210/41* (2013.01)

(58) Field of Classification Search
CPC .... G06V 10/7715; G06V 20/70; G06V 40/10; G06V 10/82; G06V 10/22; G16H 30/40; G06T 11/00; G06T 2210/21; G06T 2210/41
See application file for complete search history.

(56) References Cited

U.S. PATENT DOCUMENTS

| | | | |
|---|---|---|---|
| 10,568,600 B2 | 2/2020 | Guntzer et al. | |
| 10,579,897 B2 * | 3/2020 | Redmon | G06V 20/35 |
| 11,386,988 B2 * | 7/2022 | Johnsson | G16H 50/20 |
| 2018/0047175 A1 | 2/2018 | Wang | |
| 2019/0013050 A1 | 1/2019 | Oh | |
| 2019/0130570 A1 * | 5/2019 | Jackson | G06T 7/0014 |

(Continued)

FOREIGN PATENT DOCUMENTS

WO    WO-2021030629 A1 *  2/2021  ........... G06T 7/0012

OTHER PUBLICATIONS

International Application No. PCT/US2022/053510 filed Dec. 20, 2022—International Search Report and Written Opinion dated Apr. 13, 2023; 15 pages.

*Primary Examiner* — Shefali D Goradia
(74) *Attorney, Agent, or Firm* — McCoy Russell LLP

(57) ABSTRACT

Various methods and systems are provided for automatically classifying a plurality of image slices using body region bounding boxes identified from a localizer image. In one embodiment, a localizer image may be mapped to a plurality of bounding boxes, corresponding to a plurality of body regions, using a trained machine learning model. Coordinates of the plurality of bounding boxes may be used to determine body region boundaries, such that the body regions are non-intersecting and coherent. The body regions identified in the localizer image may then be correlated to image slice ranges, and image slices within each image slice range may be labeled as belonging to the corresponding body region.

20 Claims, 6 Drawing Sheets

(56) References Cited

U.S. PATENT DOCUMENTS

| | | |
|---|---|---|
| 2019/0313963 A1* | 10/2019 | Hillen .................. G06V 10/764 |
| 2019/0385026 A1 | 12/2019 | Richeimer |
| 2020/0342600 A1* | 10/2020 | Sjöstrand ............... A61B 6/032 |
| 2021/0026355 A1 | 1/2021 | Chen |
| 2022/0051017 A1* | 2/2022 | Choi .................... G06V 10/764 |

* cited by examiner

METHODS AND SYSTEMS FOR IMAGE SELECTION

FIELD

Embodiments of the subject matter disclosed herein relate to medical imaging.

BACKGROUND

Imaging technologies such as CT imaging allow for non-invasive acquisition of images of internal structures or features of a subject, such as a patient. Digital CT imaging systems produce digital data which can be processed into radiographic images. In digital CT imaging systems, radiation from a source is directed toward the subject. A portion of the radiation passes through the subject and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body. In some instances, an image may capture multiple structures or regions of interest.

In conventional approaches, a plurality of image slices may be taken of an imaging subject. The plurality of image slices may correspond to different regions of the imaging subject, e.g., a first subset of the plurality of image slices may correspond to a chest of the imaging subject, whereas a second subset of the plurality of image slices may correspond to an abdomen of the imaging subject. Assigning each image slice in the plurality of image slices to a corresponding region of the imaging subject may be time consuming if performed manually, or computationally expensive if performed automatically, such as by using a machine learning model to classify each image slice into a most probable region. Therefore, it is generally desired to explore approaches for assigning a plurality of image slices to corresponding regions of an imaging subject, with increased computational efficiency, and without sacrificing assignment/classification accuracy.

BRIEF DESCRIPTION

The inventors herein disclose systems and methods which at least partially address the above issues. In one embodiment, a method for identifying a plurality of image slices corresponding to a target region of an imaging subject comprises, receiving a localizer image of an imaging subject, extracting a plurality of features from the localizer image, mapping the plurality of features to coordinates defining one or more bounding boxes for one or more pre-determined regions of the imaging subject, resolving borders of the one or bounding boxes to produce a plurality of non-intersecting regions, and responding to a region of the plurality of non-intersecting regions being the target region by, correlating coordinates of the region from a coordinate system of the localizer image to a coordinate system of the plurality of image slices to produce a target image slice coordinate range, and labeling a subset of the plurality of image slices as belonging to the target region of the imaging subject based on the target image slice coordinate range. In this way, assignment of a plurality of image slices to a corresponding target region of an imaging subject may be performed using substantially a single localizer image, thereby reducing the computational complexity of the image slice classification. Further, by resolving borders of the one or more bounding boxes to produce a plurality of non-intersecting regions, assignment conflicts for image slice assignment may be avoided.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
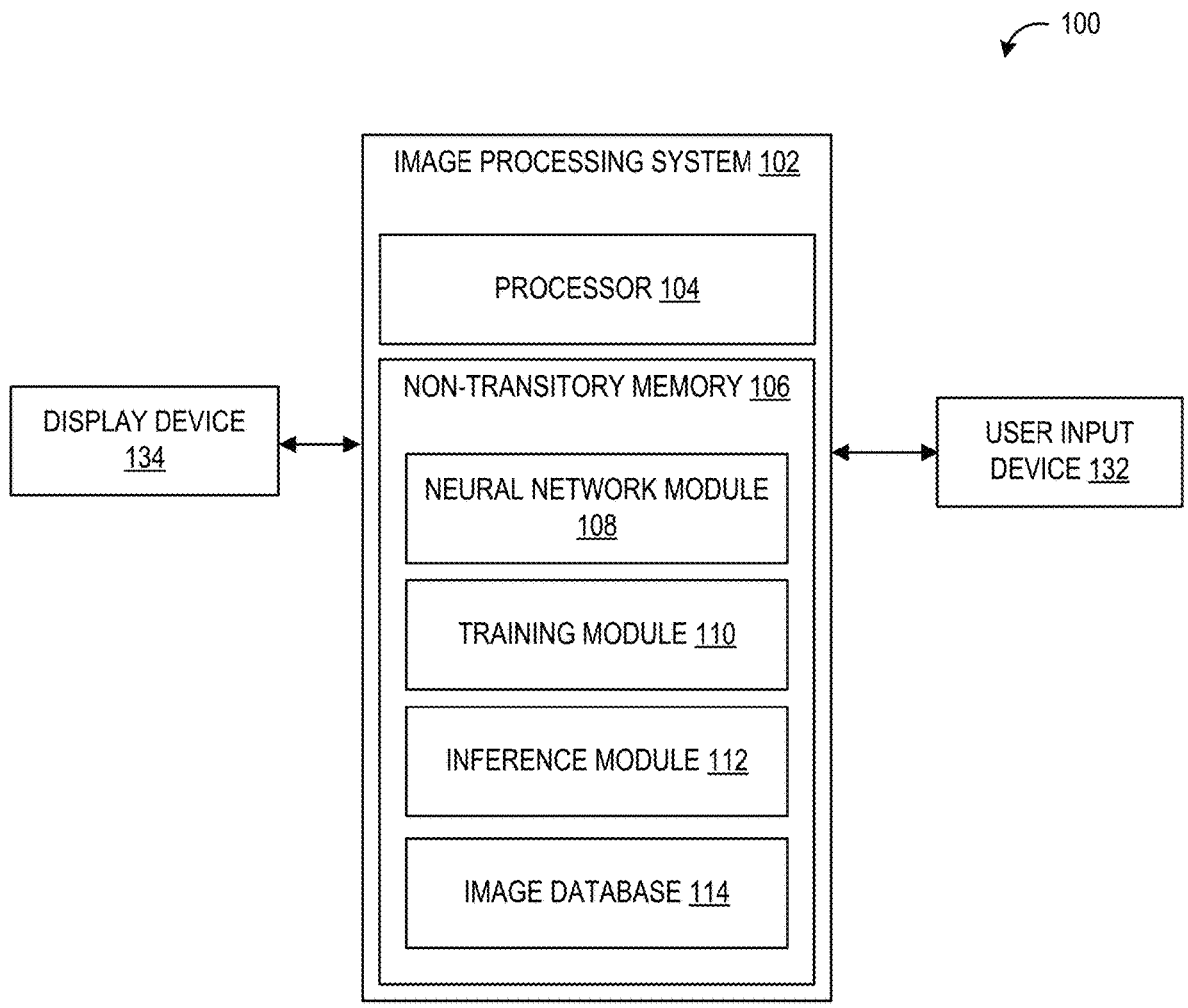
FIG. 1 shows a block diagram of an exemplary embodiment of an image processing system.

The following description relates to various embodiments of a method for training and implementing a deep learning model to identify axial slices of a target region.

A computed tomography (CT) exam combines different series of CT images taken from different angles around the body and uses computer processing to create, for example, an axial series (e.g., cross-sectional images) and a localizer series (anterior-posterior (AP) projections and lateral projections). An AP projection, herein referred to as an AP localizer, is a coronal cut and a lateral projection is a sagittal cut. The coronal cut (e.g., the AP localizer) may thus include a plurality of cross-sectional images (e.g., the axial series). The axial series includes hundreds of coronal (e.g., axial) cuts, in one example, which may be used by a radiologist or other healthcare provider to make a diagnosis.

Methods exist to define an image quality and/or for computation of CT doses of a given organ or anatomical region based on CT exams. These methods include automatically detecting an anatomical region (e.g., head, shoulders, chest, abdomen, pelvis, legs) to focus processing on the anatomical region of interest and reduce resources used compared to processing an entire patient body (e.g., all anatomical regions). Anatomical regions include axial series (e.g., multiple cross-sectional images of the anatomical region). An axial series may be directly used (e.g., images slices may be examined) to detect body regions and identify organs in the slices. However, this strategy may be time consuming due to the number of image slices in the axial series. Each image slice may be identified, detection may be individually run, and detection results may be used to examine the axial series and identify a target region.

To increase an efficiency of detecting body regions, a method is desired for identifying and analyzing one image of the axial series (e.g., a localizer) instead of analyzing all images of the axial series. The inventors herein propose a method for using an AP localizer for body region detection. In this way, a location range (e.g., coordinates) of the target region may be calculated using a patient coordinate system. Once the location range of the target region has been identified, a desired axial slice may be selected for further examination. For example, the desired axial slice may contain a structure of interest, such as an organ or an implanted medical device. Selection of the desired axial slice may be used in organ dosage calculations, to determine image capture efficiency, to assist in making a diagnosis, and so on. The method described herein may be updatable and able to be performed for multiple modalities and on multiple manufacturers (e.g., multiple imaging systems). Updates may be made as manual corrections by a user or by re-training the model using newly annotated data.

The method is based on a deep learning model, where anatomical regions of interest are identified using bounding boxes and confidence scores. The model is built with a pre-trained model where annotated data from different manufacturers and devices are used to make the pre-trained model more robust (e.g., trained on different iterations of anatomical regions, such as from different patients). A trained model is then implemented to identify region boarders for each anatomical region of an image (e.g., AP localizer) and overlay bounding boxes on the image to separate anatomical regions with a continuous partition. After selection of an anatomical region or regions of interest, inference may be performed where equivalence is determined between coordinates of region borders within the selected localizer series and a slice location to define which axial slices are included in the detected anatomical region.

Automatic detection is performed on one image, for example, the AP localizer, and may be performed without information, such as image data, for regions other than the selected anatomical region. A workflow of the herein described method is split into three steps: image normalization, automatic detection of the region with a deep learning model, and computation of region borders from the detected region and connection of each slide (e.g., from the axial series) to an anatomical region.

In this way, the method for detection of anatomical regions using a trained deep learning model may be used to compute organ dose for a CT acquisition of the anatomical region(s). Using a trained deep learning model which may be updated by a user or by further training may decrease manual selection of anatomical regions and subsequent corrections by users. Additionally, an image quality of a range of slices within the detected anatomical region may be determined using the method described herein, as boundaries of anatomical regions may be determined and, instead of processing each slice to determine an anatomical region, a single AP localizer image is used to define the anatomical region and image quality thereof can be determined.

Figure 2A:
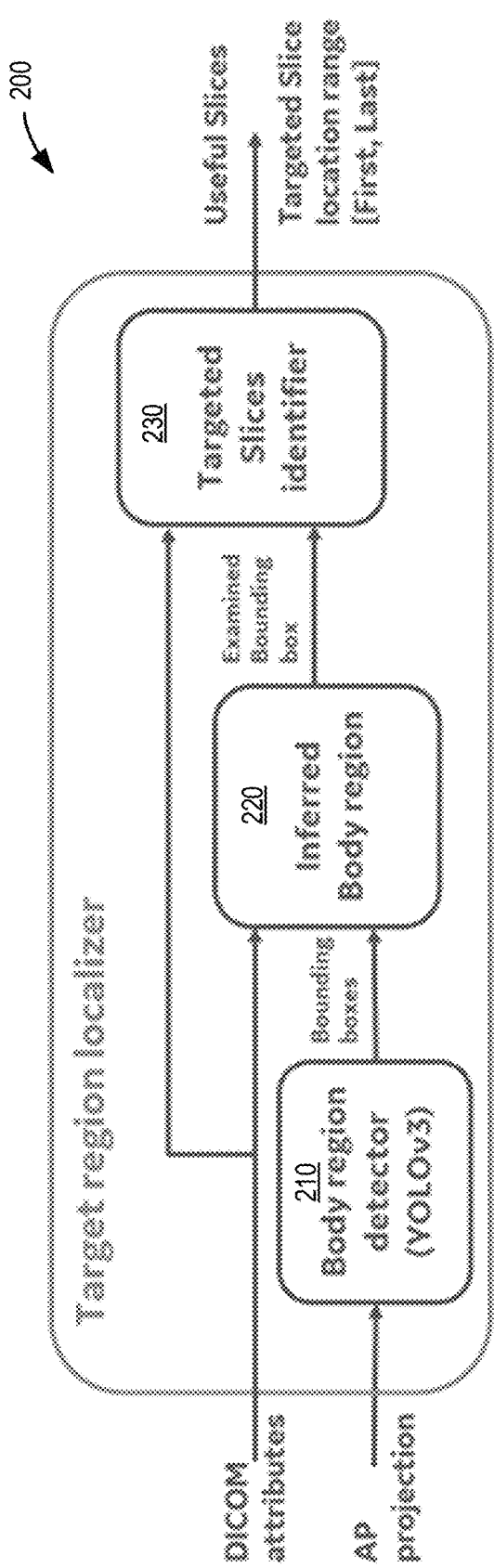
FIGS. 2A and 2B shows a workflow for a model trained to identify axial slices including a target region.
Figure 2B:
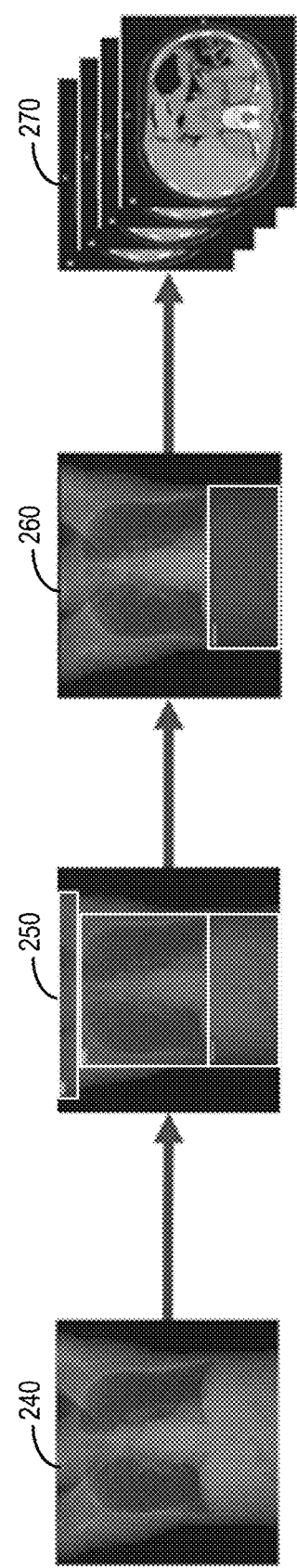
Figure 3:
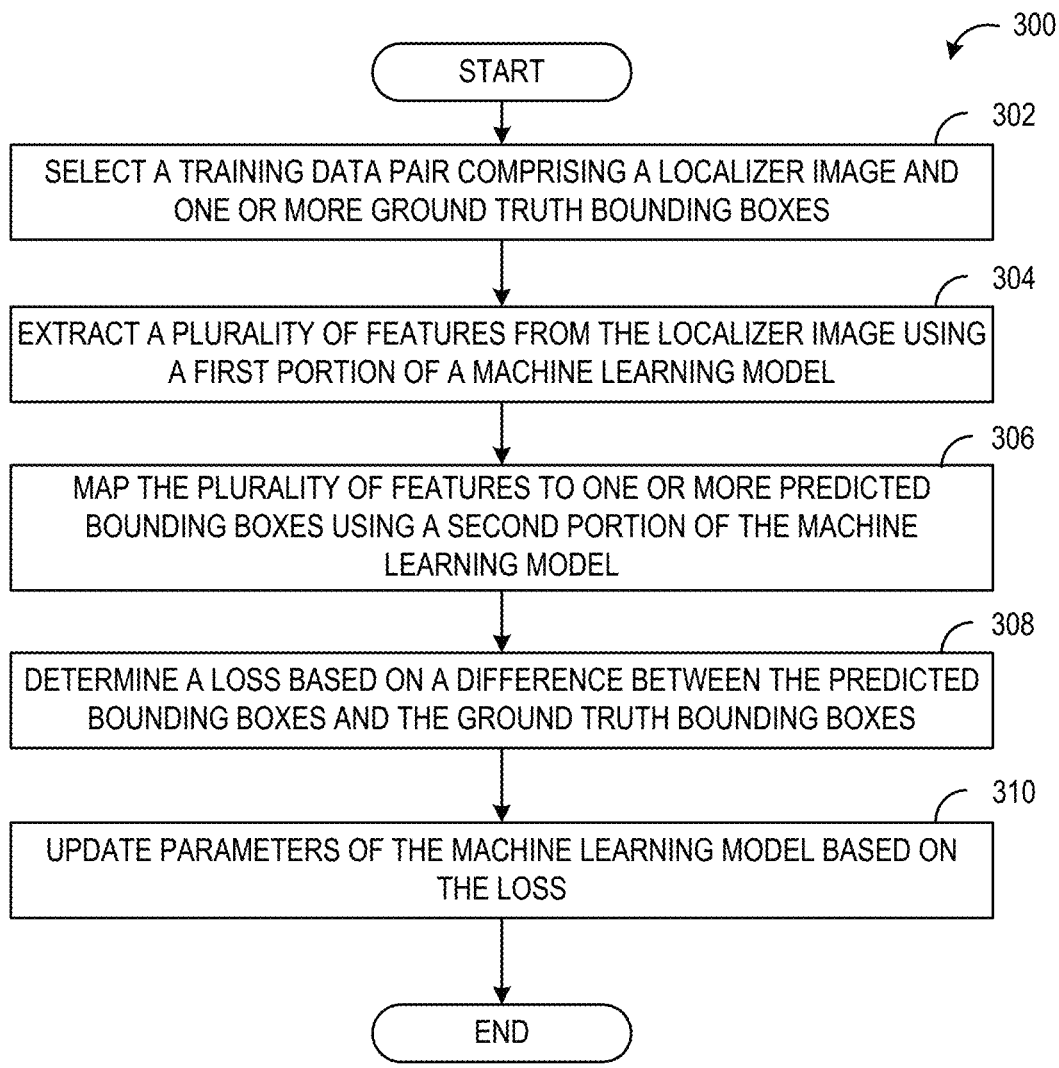
FIG. 3 shows a flow chart of a method for training a deep learning model to map localizer images to bounding boxes of one or more body regions.
Figure 4:
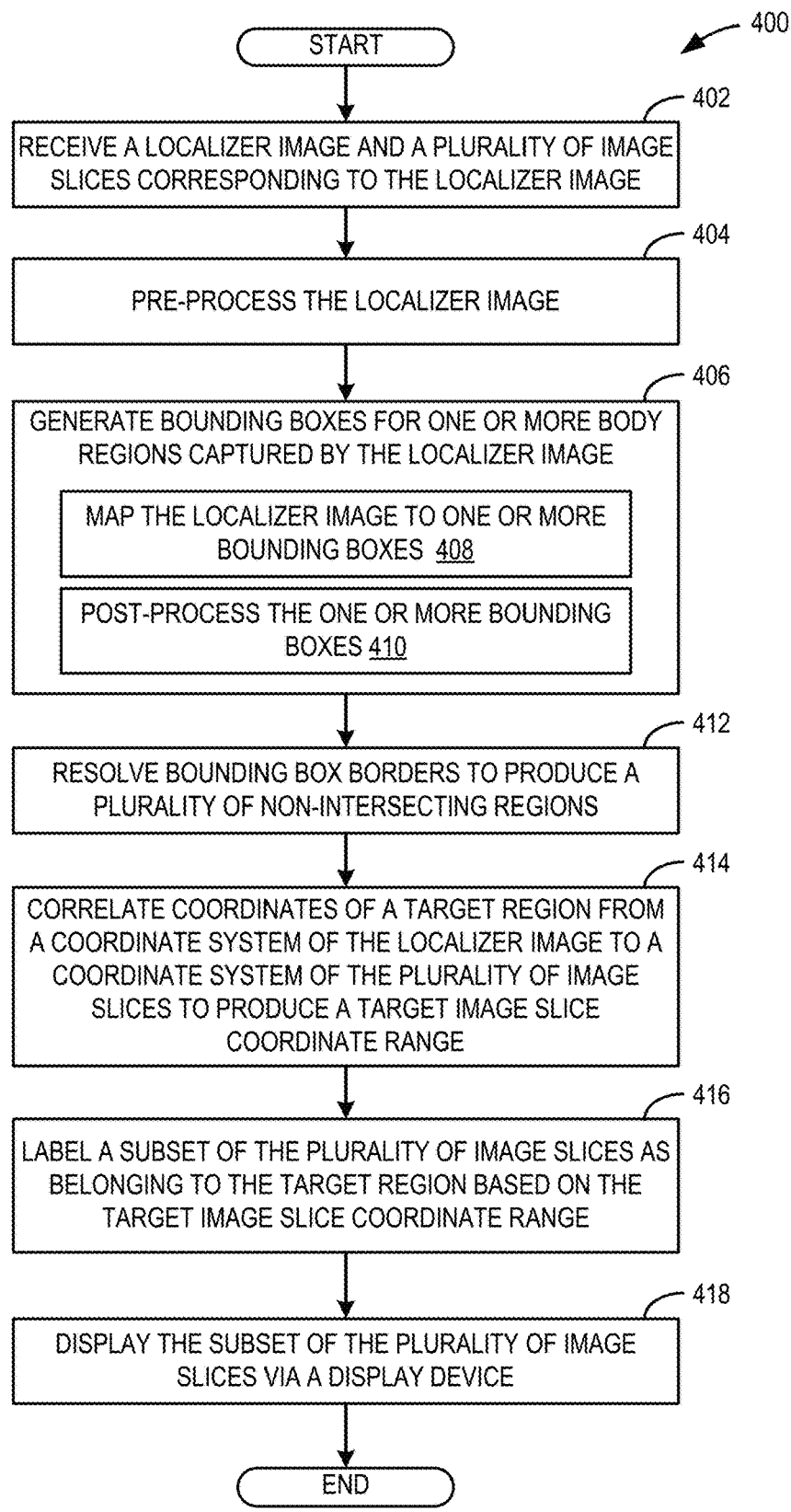
FIG. 4 shows a flow chart of a method for classifying a plurality of image slices using a single localizer image.
Figure 5:
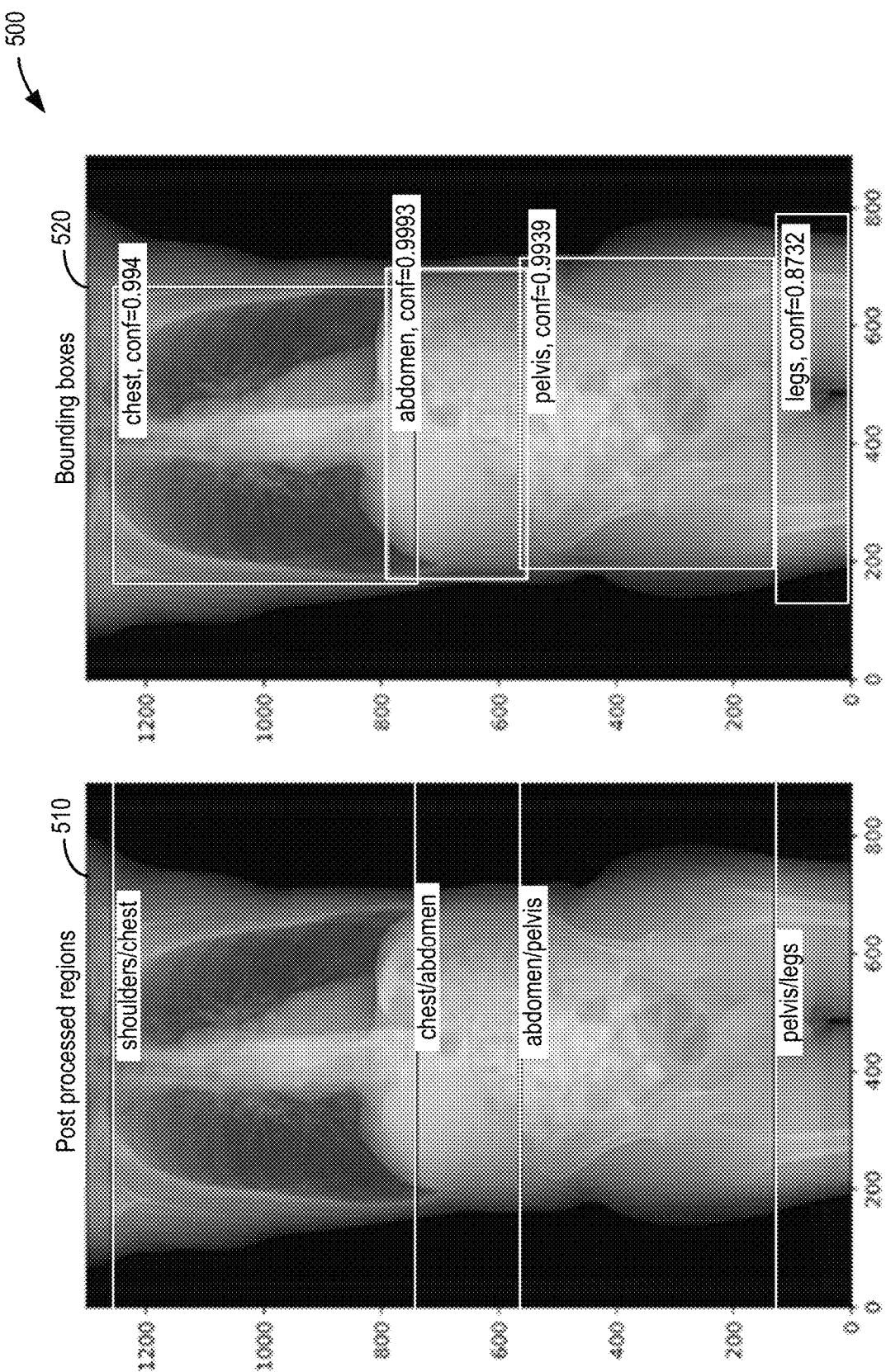
FIG. 5 shows an example image with post processed regions and bounding boxes, as generated via the method of FIG. 4.
Figure 6:
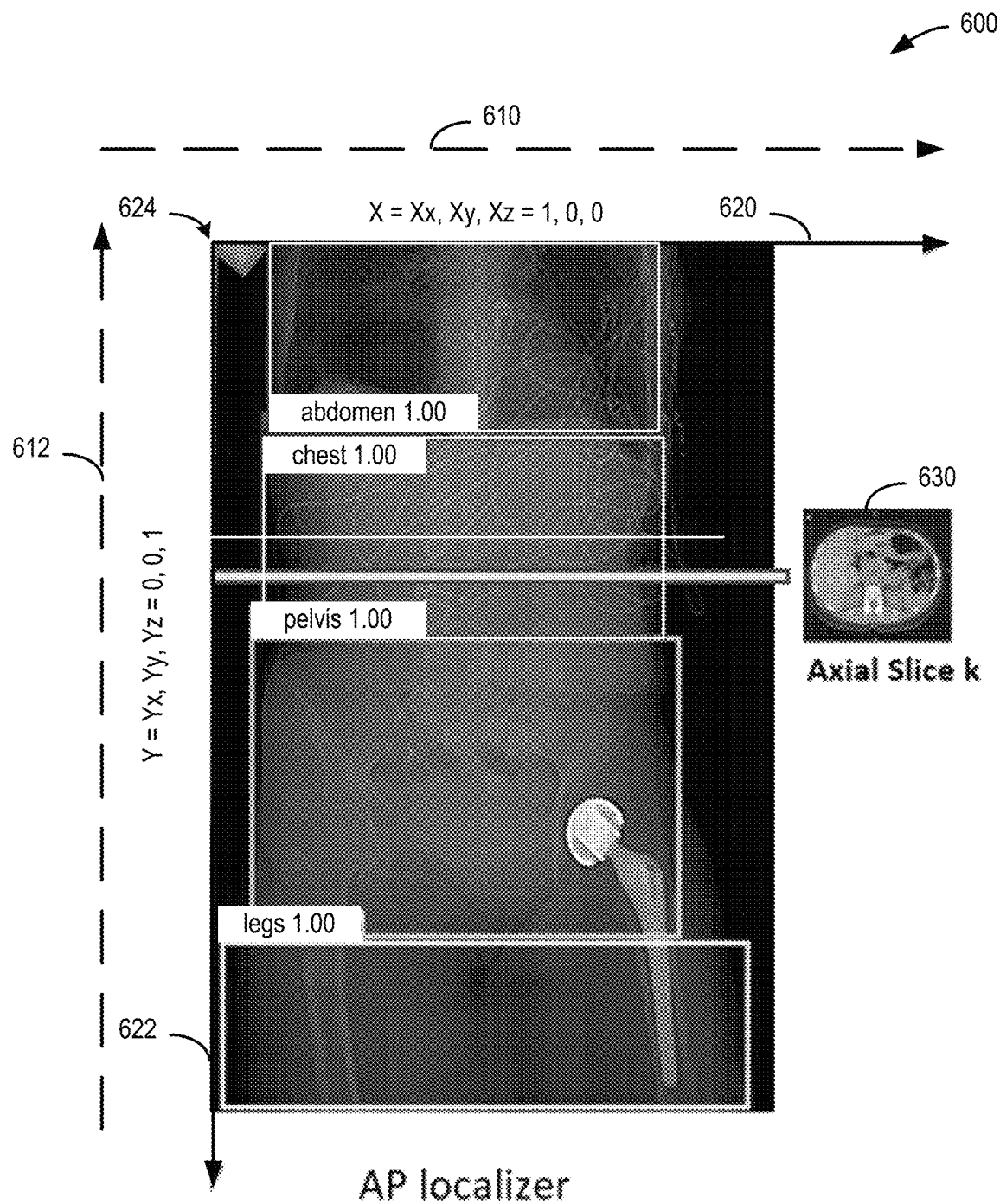
FIG. 6 shows an example image wherein the method of FIG. 4 has been implemented to identify an axial slice.

A block diagram of an exemplary embodiment of an image processing system is shown in FIG. 1. The image processing system of FIG. 1 includes a neural network module configured with a neural network, such as deep learning model, a convolutional neural network, or other neural network which may be trained and deployed by modules of the image processing system to output an axial slice of an AP localizer. The neural network may thus be herein referred to as a target region localizer. A high-level workflow describing methods for training and implementing the target region localizer is shown in FIG. 2A. FIG. 2B shows images with annotations, including bounding boxes, corresponding to steps of the target region localizer workflow. An example method for training the target region localizer is shown in FIG. 3. An example method for implementing a trained target region localizer to generate bounding boxes is shown in FIG. 4. FIG. 5 shows an example image with post processed regions and bounding boxes, as generated via the method of FIG. 4. FIG. 6 shows an example image wherein the method of FIG. 4 has been implemented to identify an axial slice.

FIG. 1 shows a block diagram 100 of an exemplary embodiment of an image processing system 102 in accordance with an embodiment. In some embodiments, image processing system 102 is incorporated into an CT imaging system. For example, image processing system 102 may be provided in an CT imaging system as a processor and memory of the CT imaging system. In some embodiments, at least a portion of image processing system 102 is disposed at a device (e.g., edge device, server, etc.) communicably coupled to the CT imaging system via wired and/or wireless connections. In some embodiments, at least a portion of image processing system 102 is disposed at a separate device (e.g., a workstation) which can receive images from the CT imaging system or from a storage device which stores the images/data generated by the CT imaging system. Image processing system 102 may be operably/communicatively coupled to a user input device 132 and a display device 134. User input device 132 may comprise a user interface of an CT imaging system while display device 134 may comprise a display device of the CT imaging system, at least in some examples. In some embodiments, user input device 132 and display device 134 may be disposed at a separate device (e.g., a workstation) which can receive images from the CT imaging system or from a storage device which stores the images/data generated by the CT imaging system.

Image processing system 102 includes a processor 104 configured to execute machine readable instructions stored in non-transitory memory 106. Processor 104 may be single core or multi-core, and the programs executed thereon may be configured for parallel or distributed processing. In some embodiments, processor 104 may optionally include individual components that are distributed throughout two or more devices, which may be remotely located and/or configured for coordinated processing. In some embodiments, one or more aspects of processor 104 may be virtualized and executed by remotely-accessible networked computing devices configured in a cloud computing configuration.

Non-transitory memory 106 may store a neural network module 108, a training module 110, an inference module 112, and an image database 114. Neural network module 108 may include at least one deep learning model, such as a CNN, and instructions for implementing the deep learning model to output bounding boxes for one or more body regions, wherein a bounding box may include a position (e.g., centroid location), a size (e.g., a height and width), a class (e.g., a body region), and a confidence score (e.g., an objectness value indicating the probability that the bounding box includes an object). Neural network module 108 may include trained and/or untrained neural networks and may further include various data, or metadata pertaining to the one or more neural networks stored therein.

Non-transitory memory 106 may further store a training module 110, which may comprise instructions for training one or more of the neural networks stored in neural network module 108. Training module 110 may include instructions that, when executed by processor 104, cause image processing system 102 to conduct one or more of the steps of method 300 for training a neural network model to inference bounding boxes for one or more body regions captured by localizer images, discussed in more detail below in reference to FIG. 3. In some embodiments, training module 110 may include instructions for implementing one or more gradient descent algorithms, applying one or more loss functions, and/or training routines, for use in adjusting parameters of one or more neural networks of neural network module 108. Training module 110 may include training datasets for the one or more neural networks of neural network module 108. Training module 110 may be located on a different device than the image processing system, for example, an edge device, server, or workstation communicatively coupled with the image processing system.

Non-transitory memory 106 also stores an inference module 112. Inference module 112 may include instructions for deploying a trained deep learning model to map localizer images to bounding boxes of one or more body regions. In particular, inference module 112 may include instructions that, when executed by processor 104, cause image processing system 102 to conduct one or more of the steps of the method 400 of FIG. 4, as described in further detail below.

Non-transitory memory 106 further stores image database 114. Image database 114 may include, for example, CT images acquired via a CT imaging system. Image database 114 may include one or more training sets for training the one or more neural networks of neural network module 108. In some embodiments, the image database may store a localizer image and a plurality of image slices corresponding to the localizer image, wherein data and metadata of the localizer and the plurality of image slices may be stored therein. In one example, image database 114 may store a plurality of image slices, indexed according to position along an axis of a patient coordinate system (also referred to herein as a reference coordinate system). The image database 114 may be located on a different device than the image processing system, for example, an edge device, server, or workstation communicatively coupled with the image processing system.

In some embodiments, non-transitory memory 106 may include components disposed at two or more devices, which may be remotely located and/or configured for coordinated processing. In some embodiments, one or more aspects of non-transitory memory 106 may include remotely-accessible networked storage devices configured in a cloud computing configuration.

User input device 132 may comprise one or more of a touchscreen, a keyboard, a mouse, a trackpad, a motion sensing camera, or other device configured to enable a user to interact with and manipulate data within image processing system 102. In one example, user input device 132 may enable a user to make a selection of an image to use in training a machine learning model, or for further processing using a trained machine learning model.

Display device 134 may include one or more display devices utilizing virtually any type of technology. In some embodiments, display device 134 may comprise a computer monitor, and may display medical images. Display device 134 may be combined with processor 104, non-transitory memory 106, and/or user input device 132 in a shared enclosure, or may be peripheral display devices and may comprise a monitor, touchscreen, projector, or other display device known in the art, which may enable a user to view CT images produced by a CT imaging system, and/or interact with various data stored in non-transitory memory 106.

It should be understood that image processing system 102 shown in FIG. 1 is for illustration, not for limitation. Another appropriate image processing system may include more, fewer, or different components.

FIG. 2A shows a workflow for a model 200 trained to identify axial slices including a target region of an AP localizer. The model 200 may be comprised of three modules: a body region detector module 210, an inference module 220, and a coordinate converting module 230. The body region detector module may be, in one example, YOLOv3. However, other modules may be used for real-time object detection. The inference module may be used to select a desired (e.g., inferred) body region. The coordinate converting module, also referred to as a targeted slices identifier, may be used to convert a location of the target region from an image coordinate system to a patient coordinate system.

YOLOv3 may be use for real-time object detection, wherein YOLOv3 uses features learned by a deep convolutional neural network (CNN) to detect an object. Predictions, including object locations and classes, are made from a single network (e.g., the CNN). The CNN may be trained end-to-end to increase accuracy. Additionally, YOLOv3 may be optimized to generalize from natural images to other domains, when compared to other object detection methods. Region proposal methods may be implemented to direct a YOLOv3 to operate within a specified region. YOLOv3 may thus operate on the whole image within the prediction boundaries and demonstrates fewer false positives, compared to other object detection methods, in background areas. YOLOv3 further detects one object per grid cell, which may enforce spatial diversity in making predictions. As a multi-scale training method, YOLOv3 may be configured to generate prediction boxes at three different scales. Therefore, YOLOv3 may be invariant to an input image size and may be able to predict small, medium, or large objects.

Real-time object detection, as done by the YOLOv3 model, comprised of a multi-scale feature extractor (e.g., CNN) and a multi-scale feature detector, may comprise five steps. YOLOv3 may take an image and split it into a grid, then identify three bounding boxes for each cell of the grid. For each of the bounding boxes, the network outputs a class probability (e.g., is the bounding box of a head region, a shoulder region, a chest region, an abdomen region, a pelvis region, or a legs region). The bounding boxes having a class probability above a threshold value are selected. The image may be filtered out in order to identify correct box containing the target region using a non-max suppression. For example, YOLOv3 may take in a 416×416 image. The image may be input into the CNN (e.g., feature extractor) to obtain feature embeddings at three different scales. Feature embeddings are then fed into three branches of the multi-scale feature detector, which outputs bounding boxes and class information for the image.

FIG. 2B shows example results of each module of the model 200 of FIG. 2A. An AP projection 240 (e.g., the AP localizer) is input into the body region detector module 210. The body region detector outputs the AP projection overlaid with bounding boxes 250 and class information. Additional DICOM attributes are input into the inference module 220 along with the AP projection with bounding boxes 250, and the inferred body region is identified. Image 260 shows a pelvis region has been highlighted as the inferred body region. The pelvis region bounding box is further examined by coordinate converting module 230 to identify targeted slices. Location ranges (e.g., coordinates) of useful slices, such as axial slices 270 containing the target region, are output by the model 200.

Turning to FIG. 3, a flowchart of an example method 300 for training a machine learning model to infer bounding boxes (e.g., to infer bounding box classes, coordinates, and confidence scores) for one or more body regions in localizer images, is shown. Method 300 may be executed by one or more of the systems discussed above. In some embodiments, method 300 may be implemented by image processing system 102 shown in FIG. 1. In some embodiments, method 300 may be implemented by training module 110, stored in non-transitory memory 106.

It will be appreciated that method 300, as well as the other methods disclosed herein, are compatible with various architectures of machine learning models. In some embodiments, a machine learning model may comprise a first portion, configured to extract features from an input localizer image, and a second, downstream portion, configured to map features extracted by the first portion (e.g., feature maps) to bounding box coordinates, classes, and confidence scores. In some embodiments, the first portion may include one or more convolutional layers, and the second portion may include one or more fully connected layers. In some embodiments, the machine learning model used herein may be a You-Only-Look-Once (YOLO) model, such as YOLOv2, YOLOv3, etc. It will be appreciated that the above machine learning model architectures are exemplary, and other model architectures are encompassed by the current disclosure.

Method 300 begins at operation 302, wherein a training data pair is selected from a plurality of training data pairs. In some embodiments, a training data pair comprises a localizer image and one or more corresponding ground truth bounding boxes. The one or more ground truth bounding boxes may be produced by a human annotator, and represent encoded human expertise on body region detection. Ground truth bounding boxes may include bounding box coordinates (e.g., height, width, centroid, or $Y_{min}$, $Y_{max}$, $X_{min}$, $X_{max}$) as well as class information (e.g., is the bounding box of a head region, a shoulder region, a chest region, an abdomen region, a pelvis region, or a legs region).

The training data pair may be intelligently selected by the computing system based on one or more pieces of metadata associated with the training data pair. In some embodiments, at operation 302, the computing system may select a training data pair from training module 110 based on one or more attributes of the localizer image of the training data pair, such as the imaging modality used to acquire the localizer image (e.g., MRI, CT) and an orientation of the localizer image (e.g., anterior-posterior, or lateral). In some embodiments, the training data pair may be acquired via communicative coupling between the computing system and an external storage device, such as via Internet connection to a remote server.

At operation 304, the computing system extracts a plurality of features from the localizer image using a first portion of the machine learning model. The first portion of the machine learning model may be referred to as a feature extractor. In some embodiments the first portion of the machine learning model may comprise one or more convolutional layers, as well as one or more pooling layers. The plurality of features extracted by the first portion of the machine learning model may be in the form of a feature map, wherein spatial relationships between extracted features are preserved. In some embodiments, feature maps at multiple scales may be produced at operation 304, that is, feature maps of difference spatial resolutions. In one embodiment, feature maps at three distinct resolutions may be produced at operation 304.

At operation 306, the computing system maps the plurality of features to one or more predicted bounding boxes using the second portion of the machine learning model. In embodiments where multiple scales of feature maps are produced by the feature extractor, operation 306 includes inputting each of the distinct feature maps into a corresponding object detector branch of the second portion of the machine learning model. The plurality of features extracted from the localizer image at operation 304 may be fed to the one or more object detection branches of the second portion of the machine learning model and propagated through one or more hidden layers, wherein output from the one or more layers is fed to an output layer. The output layer of the second portion may output the coordinates of the one or more predicted bounding boxes, as well as a class assignment for the one or more bounding boxes, and confidence scores/objectness values for the one or more predicted bounding boxes.

At operation 308, the image processing device may calculate a loss for the machine learning model based on a difference between the predicted bounding boxes and the ground truth bounding boxes. The loss may comprise multiple components, including a first component based on a difference in the position of the predicted bounding boxes versus the ground truth bounding boxes, a second component based on a difference in size between the predicted bounding boxes and the ground truth bounding boxes, a third component based on a difference between the predicted class(es) of the bounding boxes and the class(es) of the ground truth bounding boxes, as well as a fourth component based on objectness/confidence of the predicted bounding boxes versus the ground truth bounding boxes (e.g., if a bounding box is predicted for a location without a corresponding ground truth bounding box, the ground truth objectness is 0 for the location, and the predicted objectness of the location is non-zero, therefore a difference between the model prediction and the ground truth labels exists, and may be used to calculate a loss). In some embodiments, a mean-squared error may be used to determine the first and second loss components, and a binary cross entropy may be used to calculate the third and fourth components.

In embodiments wherein the machine learning model is YOLOv3, four loss functions are calculated for each bounding box: a centroid loss function (e.g., a center of the bounding box along both an x-axis and y-axis) and a width and height loss function. The centroid and width/height loss functions may each be calculated using a mean squared error (MSE) between the predicted and ground truth values. An objectness loss function includes a binary cross-entropy (BCE) of objectness score of the bounding box. A classification loss function includes a BCE of multi-class predictions of the bounding box. Loss may be calculated at three different scales, and losses are summed for backpropagation to validate the model.

At operation 310, the parameters of the machine learning model are adjusted based on the loss. The loss may be back propagated through the layers of the machine learning model to update the parameters (e.g., weights and biases) of the machine learning model. In some embodiments, back propagation of the loss may occur according to a gradient descent algorithm, wherein a gradient of the loss function (a first derivative, or approximation of the first derivative) is determined for each weight and bias of the machine learning model. Each weight (and bias) of the machine learning model is then updated by adding the negative of the product of the gradient determined (or approximated) for the weight (or bias) and a predetermined step size, according to the below equation:

$$P_{i+1} = P_i - \text{Step} \frac{\partial(\text{loss})}{\partial P_i}$$

Where $P_{i+1}$ is the updated parameter value, $P_i$ is the previous parameter value, Step is the step size, and $\partial(\text{loss})/\partial P_i$ is the partial derivative of the loss with respect to the previous parameter. In some embodiments, a gradient descent algorithm, such as stochastic gradient descent, may be used to update parameters of the machine learning model to iteratively decrease the loss.

Following operation 310, method 300 may end. It will be noted that method 300 may be repeated until the parameters of the machine learning model converge, a threshold accuracy is obtained (for the training data or for a separate validation dataset), or the rate of change of the parameters of the machine learning model for each iteration of method 300 are less than a threshold rate of change. In this way, method 300 enables a machine learning model to be trained to map localizer images to bounding boxes for one or more body regions.

In some embodiments, method 300 may be executed as part of a fine-tuning training procedure, wherein a pre-trained machine learning model is "fine-tuned" for use in a particular task (e.g., for body region detection). In some embodiments, fine-tuning may include freezing one or more parameters of the pre-trained machine learning model, wherein a frozen parameter is not updated at operation 310. By freezing parameters, catastrophic forgetting during the fine-tuning process may be avoided. In some embodiments, fine-tuning may be split into two phases: a first phase wherein parameters in the terminal one to five layers (that is, between one and five layers, starting from an output layer and progressing back towards an input layer) of the machine learning model are left unfrozen, and all other parameters are frozen; and a second phase, wherein all parameters of the machine learning model are unfrozen. The inventors herein have determined that the above split phase fine-tuning process may advantageously increase bounding box prediction accuracy, with a reduced probability of catastrophic forgetting, and with a reduced number of training data pairs.

In a particular example, a machine learning model may be pre-trained to detect objects on a generic dataset, for example, weights of the deep learning model may be trained on an ImageNet 1000 dataset. The pre-trained machine learning model may then by fine-tuned on a domain specific dataset, such as body region detection in medical images, using a two phase training process. In the first phase, all layers but the output (e.g., the three last layers) are frozen, and a method 300 is run for a pre-determined number of epochs. In the second phase, all layers are unfrozen to fine-tune weights of the model once the model has been trained. This may result in increased accuracy of model identification of anatomical regions. Additionally, the second run may include an early stop if training loss is determined to be below a threshold of acceptable loss/error.

Turning to FIG. 4, a method for assigning a plurality of image slices to one or more body region classes, is shown. Method 400 may be executed by one or more of the systems disclosed herein. In some embodiments, an image processing system may perform one or more of the operations of method 400 by executing instructions stored in non-transitory memory.

Method 400 begins at operation 402, wherein the image processing system receives a localizer image and a plurality of image slices corresponding to the localizer image.

At operation 404, the image processing system pre-processes the localizer image. In some embodiments, pre-processing may include extracting pixel intensity data from a DICOM file of the localizer image and normalizing the pixel intensity data to a pre-determined range. In some embodiments, pre-processing the localizer image may include converting the greyscale localizer image to an RGB image by duplicating pixel intensity data across three channels corresponding the red, green, and blue, color channels of a natural image. Converting the image to greyscale then to RBG is done to convert DICOM images to a useable format (e.g., RBG images, JPG format) by the YOLOv3 model or other model for image segmentation/detection. Further, black bands which may appear on pixel data may be deleted. For example, localizer images may be reformatted to fit a format of the trained machine learning model used for body region detection. For example, pixel intensity data of a localizer image may be converted from a fixed clip range [600, 1800] to a grayscale range [0, 255], and duplicated to simulate a natural RGB image to red, green, blue (RGB) with channel duplication.

At operation 406, the image processing system generates bounding boxes for one or more body regions captured by the localizer image. Operation 406 may include operation 408, wherein the image processing system maps the localizer image to one or more bounding boxes for one or more body regions. In some embodiments, bounding boxes include coordinates, labels, and confidence scores. In some embodiments, model inference is performed following image preprocessing. The preprocessed localizer image is input into a YOLOv3 model, which performs inference to generate a prediction of bounding boxes and associated body region labels. Prior to implementing the YOLOv3 model, the model may be loaded with weights determined learned during a training process, such as the training process described in FIG. 3. In some embodiments, inference output includes bounding box coordinates, labels of detected objects, and a confidence score. Bounding box coordinates may include boundaries of each bounding box, including maximum and minimum x-values and y-values of the bounding box with respect to a DICOM image coordinate system, further described below. Labels of detected objects include anatomical/body region labels, such as chest, abdomen, pelvis, and so on. The confidence score is a floating point value between zero and one, indicating a confidence of the inferred bounding box position and class label.

Operation 406 may further include operation 410, wherein the image processing system post-processes the one or more bounding boxes to produce a coherent set of bounding boxes. Coherence, as used herein, generally refers to conformity of body regions detected by a statistical model, such as a trained machine learning model, with pre-determined rules. In one example, coherence of detected body regions includes no duplicate regions (e.g., no two head regions, no to pelvis regions, etc.), as well as a pre-determined spatial ordering of body regions (e.g., body regions identified in bounding boxes conform to a pre-determined order such as that coordinates of head >shoulders>chest>abdomen>pelvis>legs). Further, coherence may include determining if one or more body region gaps exist within the one or more bounding boxes (e.g., a head bounding box and a pelvis bounding box are identified, but no chest or abdomen bounding boxes are identified). If two consecutive gaps are identified, the bounding boxes may be deemed incoherent, and method 400 may end. However, if a single gap is detected between adjacent regions, method 400 may proceed, and the missing body region may be inferred by boundaries of the adjacent body regions.

In some embodiments, operation 410 includes extracting bounding boxes and checking labels, including checking for repetition, gaps, or incorrect order. For example, if a label is present multiple times, the bounding box with the highest confidence score for the label is kept. If a single central region is missing (that is, a region with bounding regions on both ends), the algorithm checks if a discarded bounding box (e.g., from multiple present labels) may fill the gap (e.g., be a coherent position in relation to the surrounding regions and have a low IoU with other boxes).

At operation 412, the image processing system resolves bounding box borders to produce a plurality of non-intersecting regions. Following extraction of bounding boxes and post-processing, coordinates of the resulting bounding box borders are extracted. For example, coordinates of borders of interest for each bounding box are extracted. One example includes extracting coordinates for the bottom of the head box, the top of the legs box (if present) and the top and bottom coordinates for all other boxes. In some embodiments, the image processing system applies a region border algorithm to the one or more bounding boxes to clean inference results and produce non-intersecting y-coordinate borders of each anatomical region detected. Additionally, if bounding boxes overlap, application of the region border algorithm may include determining a border to separate the regions.

In one example, operation 412 may include extracting coordinates of one or more of a bottom of a head bounding box, a top of a chest bounding box, a bottom of the chest bounding box, a top of an abdomen bounding box, a bottom of the abdomen bounding box, a top of a pelvis bounding box, a bottom of the pelvis bounding box, and a top of a legs bounding box. The image processing system may then determine body region borders if at least one of the considered borders is present, by setting a head/shoulder boundary as the bottom of the head bounding box, setting a shoulder/chest boundary as the top of the chest bounding box, setting a chest/abdomen boundary as a lesser of the bottom of the chest bounding box and the top of the abdomen bounding box, setting an abdomen/pelvis boundary as the top of the pelvis bounding box, if the pelvis bounding box is present, else setting the abdomen/pelvis boundary as the bottom of the abdomen bounding box, and setting a pelvis/leg boundary as a lesser of the bottom of the pelvis bounding box and the top of the legs bounding box.

At operation 414, the image processing system correlates coordinates of a target region from a coordinate system of the localizer image to a coordinate system of the plurality of image slices to produce a target image slice coordinate range. In some embodiments, correlating coordinates of the region from the coordinate system of the localizer image to the coordinate system of the plurality of image slices to produce the target image slice coordinate range, comprises, mapping a first boundary and a second boundary of the region from a first axis in the coordinate system of the localizer image, to a second axis in the coordinate system of the plurality of image slices, to produce the target image slice coordinate range, wherein the plurality of image slices are indexed based on distance along the second axis, and wherein distance along the first axis is measured in pixels, and distance along the second axis is measured in millimeters. In one example, a relationship between distance along the first axis and distance along the second axis is given by:

$$Z_k = Z_{ref} + Y_k * \text{Spacing}_{\frac{Z}{Y}} * \cos\theta$$

where $Z_k$ is a distance of a point k along the second axis, $Z_{ref}$ is an offset between an origin of the first axis and an origin of the second axis, $Y_k$ is a distance of the point k along the first axis, $\text{Spacing}_{\frac{Z}{Y}}$ is a ratio between distance along the second axis and distance along the first axis, and $\theta$ is an angle between the first axis and the second axis, wherein when $\theta$ equals 0, the first axis is parallel to the second axis.

At operation 416, the image processing system labels a subset of the plurality of image slices as belonging to the target region based on the target image slice coordinate range. Operation 416 may be repeated for each distinct region identified at operation 412, thereby classifying each of the plurality of image slices into a corresponding body region category.

At operation 418, the image processing system displays the subset of the plurality of image slices via a display device. In this way, a user may view a subset of a plurality of image slices which belong to an anatomical class of interest, e.g., a radiologist may wish to inspect images belonging to an abdomen of an imaging subject. By automatically labeling each of the plurality of image slices according to regions identified in a localizer image, selection and display of images of interest may be performed without manual review, and in a manner computationally more efficient than separate classification of each of the plurality of image slices (e.g., by inputting each of the plurality of image slices into a machine learning model and outputting separate body region labels for each image slice). Further, by performing region identification on a localizer image, and by resolving boundaries of the regions such that regions are coherent and non-intersecting, an accuracy of the image slice classification may be increased, and errors such as non-contiguous image slices being classified to a same body region may be avoided.

FIG. 5 shows embodiments 500 of an AP localizer image including post processed regions and bounding boxes as determined according to the method of FIG. 4. A first image 510 shows regions of the AP localizer image identified by pre-processing of the AP localizer image, such as described at operation 404 of method 400, with anatomical regions labeled by horizontal lines across the image, segmenting the regions. The same AP localizer image is shown in a second image 520, where anatomical regions are shown by bounding boxes including labels and confidence scores having been determined, for example, at operation 406 of method 400.

FIG. 6 shows an AP localizer image to which the model is applied to select an axial slice. A patient/reference coordinate system in mm is shown by dashed lines. A first dashed line 610 is an x-axis and a second dashed line 612 is a z-axis of the patient/reference coordinate system. The patient/reference coordinate system is the coordinate system of the plurality of axial image slices. A DICOM image coordinate system, where units are pixels, is shown by solid lines. A first solid line 620 is an x-axis and a second solid line 622 is a y-axis of the DICOM image coordinate system. The DICOM image coordinate system is the coordinate system of the localizer image. A zero point of the DICOM image coordinate system is at point 624, where DICOM image coordinates are (0, 0) and patient/reference coordinates are (x_ref, z_ref).

DICOM attributes from the AP localizer are converted from bounding box heights (e.g., values of the y-axis shown by the second solid line 622 of the DICOM image coordinate system) to a slice location range (e.g., values along the z-axis shown by the second dashed line 612 of the patient/reference coordinate system).

A targeted slices identifier function is used to calculate a slice location (slice location(k)) of an axial slice k 630. Inputs to the function include pixel spacing (pixel spacing$_{AP}$), image orientation (Image Orientation(Patient)$_{AP}$), and image position (Image Position(Patient)$_{AP}$).

$$\text{Slice location}(k) = z_{ref} + (Y(k) * z_{orientation} * \text{pixel spacing}_{AP}) \quad (1)$$

For axial slice k 630, equation 1 shows the formula to identify the corresponding y-value (e.g., k projection value along y-axis of the DICOM image coordinate system) in units of the reference coordinate system (e.g., mm). Equation 1 further includes using elements of equations 2-4.

$$\text{Image Orientation(Patient)}_{AP} = [X_x, X_y, X_z, Y_x, Y_y, Y_z] \quad (2)$$

$$\text{Image Position(Patient)}_{AP} = [x_{ref}, y_{ref}, z_{ref}] \quad (3)$$

$$Z_{orientation} = Y_z \quad (4)$$

In this way, coordinates of a region of interest from a coordinate system of the localizer image may be correlated to a coordinate system of the plurality of image slices to identify coordinates of the axial slice k 630 according to the method 400 described above and equations 1-4. As described in FIGS. 2 and 4, the method may be implemented to identify location ranges (e.g., coordinates) of useful slices, such as axial slices containing the target region.

The disclosure also provides support for a method comprising: receiving a localizer image of an imaging subject and a plurality of image slices corresponding to the localizer image, extracting a plurality of features from the localizer image, mapping the plurality of features to one or more bounding boxes for one or more pre-determined regions of the imaging subject using a trained machine learning model, resolving boundaries of the one or more bounding boxes to produce a plurality of non-intersecting regions, and responding to a region of the plurality of non-intersecting regions being a target region by: correlating coordinates of the region from a coordinate system of the localizer image to a coordinate system of the plurality of image slices to produce a target image slice coordinate range, and labeling a subset of the plurality of image slices as belonging to the target region of the imaging subject based on the target image slice coordinate range. In a first example of the method, the one or more bounding boxes include one or more of a head bounding box, a chest bounding box, an abdomen bounding box, a pelvis bounding box, and a leg bounding box. In a second example of the method, optionally including the first example, resolving boundaries of the one or more bounding boxes to produce the plurality of non-intersecting regions, comprises one or more of: setting a head/shoulder boundary as a bottom of the head bounding box, setting a shoulder/chest boundary as a top of the chest bounding box, setting a chest/abdomen boundary as a lesser of a bottom of the chest bounding box and a top of the abdomen bounding box, setting an abdomen/pelvis boundary as a top of the pelvis bounding box, if the pelvis bounding box is present, else setting the abdomen/pelvis boundary as the bottom of the abdomen bounding box, and setting a pelvis/leg boundary as a lesser of a bottom of the pelvis bounding box and a top of the leg bounding box. In a third example of the method, optionally including one or both of the first and second examples, the plurality of non-intersecting regions include one or more of a head region, a shoulder region, a chest region, an abdomen region, a pelvis region, and a leg region. In a fourth example of the method, optionally including one or more or each of the first through third examples, correlating coordinates of the region from the coordinate system of the localizer image to the coordinate system of the plurality of image slices to produce the target image slice coordinate range, comprises, mapping a first boundary and a second boundary of the region from a first axis in the coordinate system of the localizer image, to a second axis in the coordinate system of the plurality of image slices, to produce the target image slice coordinate range, wherein the plurality of image slices are indexed based on distance along the second axis. In a fifth example of the method, optionally including one or more or each of the first through fourth examples, distance along the first axis is measured in pixels, and distance along the second axis is measured in millimeters, and wherein a relationship between distance along the first axis and distance along the second axis is given by: where is a distance of a point k along the second axis, is an offset between an origin of the first axis and an origin of the second axis, is a distance of the point k along the first axis, is a ratio between distance along the second axis and distance along the first axis, and is an angle between the first axis and the second axis, wherein when equals 0, the first axis is parallel to the second axis. In a sixth example of the method, optionally including one or more or each of the first through fifth examples the method further comprising: displaying the subset of the plurality of image slices via a display device.

The disclosure also provides support for a method, comprising: receiving a localizer image, pre-processing the localizer image to form a pre-processed image based on an architecture of a trained machine learning model, mapping the pre-processed image to one or more bounding boxes, resolving boundaries of the one or more bounding boxes to produce a plurality of non-intersecting regions, and classifying a plurality of axial images into one or more classes based on the plurality of non-intersecting regions. In a first example of the method, the localizer image and the plurality of axial images are acquired via a CT scanner. In a second example of the method, optionally including the first example, pre-processing the localizer image comprises: extracting pixel intensity data from the localizer image, normalizing the pixel intensity data to a pre-determined range, and duplicating the normalized pixel intensity data into three channels, corresponding to RGB channels of a natural image. In a third example of the method, optionally including one or both of the first and second examples, the trained machine learning model is YOLOv3. In a fourth example of the method, optionally including one or more or each of the first through third examples, classifying the plurality of axial images comprises: selecting at least one region of the plurality of non-intersecting regions, extracting coordinates of the at least one region, converting coordinates of the at least one region into a slice location range, and assigning each image slice within the slice location range to the at least one region.

The disclosure also provides support for a system comprising: a non-transitory memory, wherein the non-transitory memory stores instructions, and a trained machine learning model, a display device, and a processor, wherein the processor is communicably coupled to the non-transitory memory and the display device, and wherein the processor, when executing the instructions, is configured to: receive a localizer image of an imaging subject and a plurality of image slices corresponding to the localizer image, map the localizer image to one or more bounding boxes using the trained machine learning model, post-process the one or more bounding boxes to produce a coherent set of bounding boxes, resolve boundaries of the coherent set of bounding boxes to produce a plurality of non-intersecting regions, correlate coordinates of a region of the plurality of non-intersecting regions from a coordinate system of the localizer image to a coordinate system of the plurality of image slices to produce a image slice coordinate range, label a subset of the plurality of image slices as belonging to the region of the imaging subject based on the image slice coordinate range, and displaying the subset of the plurality of image slices via the display device. In a first example of the system, the processor is configured to post-process the one or more bounding boxes to produce the coherent set of bounding boxes by: responding to detection of a first bounding box assigned to a first body region, and a second bounding box also assigned to the first body region by: keeping the first bounding box in response to a determination that the first bounding box has a higher confidence score than the second bounding box, and discarding the second bounding box. In a second example of the system, optionally including the first example, the processor is further configured to post-process the one or more bounding boxes to produce the coherent set of bounding boxes by: removing duplicate bounding boxes based on a pre-determined body region order. In a third example of the system, optionally including one or both of the first and second examples, the processor is configured to resolve boundaries of the coherent set of bounding boxes to produce the plurality of non-intersecting regions, by, extracting coordinates of one or more of: a bottom of a head bounding box, a top of a chest bounding box, a bottom of the chest bounding box, a top of an abdomen bounding box, a bottom of the abdomen bounding box, a top of a pelvis bounding box, a bottom of the pelvis bounding box, and a top of a legs bounding box. In a fourth example of the system, optionally including one or more or each of the first through third examples, the processor is configured to resolve boundaries of the coherent set of bounding boxes to produce the plurality of non-intersecting regions, by: setting a head/shoulder boundary as the bottom of the head bounding box, setting a shoulder/chest boundary as the top of the chest bounding box, setting a chest/abdomen boundary as a lesser of the bottom of the chest bounding box and the top of the abdomen bounding box, setting an abdomen/pelvis boundary as the top of the pelvis bounding box, if the pelvis bounding box is present, else setting the abdomen/pelvis boundary as the bottom of the abdomen bounding box, and setting a pelvis/leg boundary as a lesser of the bottom of the pelvis bounding box and the top of the leg bounding box. In a fifth example of the system, optionally including one or more or each of the first through fourth examples, the processor is configured to correlate coordinates of the region of the plurality of non-intersecting regions from the coordinate system of the localizer image to the coordinate system of the plurality of image slices to produce the image slice coordinate range by: mapping a first boundary and a second boundary of the region from a first axis in the coordinate system of the localizer image, to a second axis in the coordinate system of the plurality of image slices, to produce the image slice coordinate range. In a sixth example of the system, optionally including one or more or each of the first through fifth examples, a mapping between the first axis and the second axis is given by: where is a distance of a point k along the second axis, is an offset between an origin of the first axis and an origin of the second axis, is a distance of the point k along the first axis, is a ratio between distance along the second axis and distance along the first axis, and is an angle between the first axis and the second axis. In a seventh example of the system, optionally including one or more or each of the first through sixth examples, the processor is configured to label the subset of the plurality of image slices as belonging to one of a head region, a shoulder region, a chest region, an abdomen region, a pelvis region, and a legs region.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A method comprising:
receiving a localizer image of an imaging subject and a plurality of image slices corresponding to the localizer image;
extracting a plurality of features from the localizer image;
mapping the plurality of features to one or more bounding boxes for one or more pre-determined regions of the imaging subject using a trained machine learning model;
resolving boundaries of the one or more bounding boxes to produce a plurality of non-intersecting regions by extracting boundary box borders and determining if the boundary box borders overlap; and
responding to a region of the plurality of non-intersecting regions being a target region by:
correlating coordinates of the region from a coordinate system of the localizer image to a coordinate system of the plurality of image slices to produce a target image slice coordinate range; and
labeling a subset of the plurality of image slices as belonging to the target region of the imaging subject based on the target image slice coordinate range.

2. The method of claim 1, wherein the one or more bounding boxes include one or more of a head bounding box, a chest bounding box, an abdomen bounding box, a pelvis bounding box, and a leg bounding box.

3. The method of claim 2, wherein resolving boundaries of the one or more bounding boxes to produce the plurality of non-intersecting regions, comprises one or more of:
setting a head/shoulder boundary as a bottom of the head bounding box;
setting a shoulder/chest boundary as a top of the chest bounding box;
setting a chest/abdomen boundary as a lesser of a bottom of the chest bounding box and a top of the abdomen bounding box;
setting an abdomen/pelvis boundary as a top of the pelvis bounding box, if the pelvis bounding box is present, else setting the abdomen/pelvis boundary as the bottom of the abdomen bounding box; and
setting a pelvis/leg boundary as a lesser of a bottom of the pelvis bounding box and a top of the leg bounding box.

4. The method of claim 1, wherein the plurality of non-intersecting regions include one or more of a head region, a shoulder region, a chest region, an abdomen region, a pelvis region, and a leg region.

5. The method of claim 1, wherein correlating coordinates of the region from the coordinate system of the localizer image to the coordinate system of the plurality of image slices to produce the target image slice coordinate range, comprises, mapping a first boundary and a second boundary of the region from a first axis in the coordinate system of the localizer image, to a second axis in the coordinate system of the plurality of image slices, to produce the target image slice coordinate range, wherein the plurality of image slices are indexed based on distance along the second axis.

6. A method comprising:
receiving a localizer image of an imaging subject and a plurality of image slices corresponding to the localizer image;
extracting a plurality of features from the localizer image;
mapping the plurality of features to one or more bounding boxes for one or more pre-determined regions of the imaging subject using a trained machine learning model;
resolving boundaries of the one or more bounding boxes to produce a plurality of non-intersecting regions; and
responding to a region of the plurality of non-intersecting regions being a target region by:
correlating coordinates of the region from a coordinate system of the localizer image to a coordinate system of the plurality of image slices to produce a target image slice coordinate range; and
labeling a subset of the plurality of image slices as belonging to the target region of the imaging subject based on the target image slice coordinate range,
wherein correlating coordinates of the region from the coordinate system of the localizer image to the coordinate system of the plurality of image slices to produce the target image slice coordinate range, comprises, mapping a first boundary and a second boundary of the region from a first axis in the coordinate system of the localizer image, to a second axis in the coordinate system of the plurality of image slices, to produce the target image slice coordinate range, wherein the plurality of image slices are indexed based on distance along the second axis;
wherein distance along the first axis is measured in pixels, and distance along the second axis is measured in millimeters, and wherein a relationship between distance along the first axis and distance along the second axis is given by:

$$Z_k = Z_{ref} + Y_k * Spacing_{\frac{Z}{Y}} * \cos\theta$$

where $Z_k$ is a distance of a point k along the second axis, $Z_{ref}$ is an offset between an origin of the first axis and an origin of the second axis, $Y_k$ is a distance of the point k along the first axis, $Spacing_{\frac{Z}{Y}}$ is a ratio between distance along the second axis and distance along the first axis, and $\theta$ is an angle between the first axis and the second axis, wherein when $\theta$ equals 0, the first axis is parallel to the second axis.

7. The method of claim 1, the method further comprising:
displaying the subset of the plurality of image slices via a display device.

8. A method, comprising:
receiving a localizer image;
pre-processing the localizer image to form a pre-processed image based on an architecture of a trained machine learning model;
mapping the pre-processed image to one or more bounding boxes;
resolving boundaries of the one or more bounding boxes to produce a plurality of non-intersecting regions by extracting boundary box borders and determining if the boundary box borders overlap; and
classifying a plurality of axial images into one or more classes based on the plurality of non-intersecting regions.

9. The method of claim 8, wherein the localizer image and the plurality of axial images are acquired via a CT scanner.

10. The method of claim 8, wherein pre-processing the localizer image comprises:
extracting pixel intensity data from the localizer image;
normalizing the pixel intensity data to a pre-determined range; and
duplicating the normalized pixel intensity data into three channels, corresponding to RGB channels of a natural image.

11. The method of claim 8, wherein the trained machine learning model is YOLOv3.

12. The method of claim 8, wherein classifying the plurality of axial images comprises:
selecting at least one region of the plurality of non-intersecting regions;
extracting coordinates of the at least one region;
converting coordinates of the at least one region into a slice location range; and
assigning each image slice within the slice location range to the at least one region.

13. A system comprising:
a non-transitory memory, wherein the non-transitory memory stores instructions, and a trained machine learning model;
a display device; and
a processor, wherein the processor is communicably coupled to the non-transitory memory and the display device, and wherein the processor, when executing the instructions, is configured to:

receive a localizer image of an imaging subject and a plurality of image slices corresponding to the localizer image;

map the localizer image to one or more bounding boxes using the trained machine learning model;

post-process the one or more bounding boxes to produce a coherent set of bounding boxes;

resolve boundaries of the coherent set of bounding boxes to produce a plurality of non-intersecting regions by extracting boundary box borders and determining if the boundary box borders overlap;

correlate coordinates of a region of the plurality of non-intersecting regions from a coordinate system of the localizer image to a coordinate system of the plurality of image slices to produce an image slice coordinate range;

label a subset of the plurality of image slices as belonging to the region of the imaging subject based on the image slice coordinate range; and displaying the subset of the plurality of image slices via the display device.

14. The system of claim 13, wherein the processor is configured to post-process the one or more bounding boxes to produce the coherent set of bounding boxes by:

responding to detection of a first bounding box assigned to a first body region, and a second bounding box also assigned to the first body region by:

keeping the first bounding box in response to a determination that the first bounding box has a higher confidence score than the second bounding box, the confidence score indicating probability that the respective bounding box includes an object; and discarding the second bounding box.

15. The system of claim 13, wherein the processor is further configured to post-process the one or more bounding boxes to produce the coherent set of bounding boxes by:

removing duplicate bounding boxes based on a predetermined body region order.

16. The system of claim 13, wherein the processor is configured to resolve boundaries of the coherent set of bounding boxes to produce the plurality of non-intersecting regions, by, extracting coordinates of one or more of:

a bottom of a head bounding box;
a top of a chest bounding box;
a bottom of the chest bounding box;
a top of an abdomen bounding box;
a bottom of the abdomen bounding box;
a top of a pelvis bounding box;
a bottom of the pelvis bounding box; and
a top of a legs bounding box.

17. The system of claim 16, wherein the processor is configured to resolve boundaries of the coherent set of bounding boxes to produce the plurality of non-intersecting regions, by:

setting a head/shoulder boundary as the bottom of the head bounding box;

setting a shoulder/chest boundary as the top of the chest bounding box;

setting a chest/abdomen boundary as a lesser of the bottom of the chest bounding box and the top of the abdomen bounding box;

setting an abdomen/pelvis boundary as the top of the pelvis bounding box, if the pelvis bounding box is present, else setting the abdomen/pelvis boundary as the bottom of the abdomen bounding box; and setting a pelvis/leg boundary as a lesser of the bottom of the pelvis bounding box and the top of the legs bounding box.

18. The system of claim 13, wherein the processor is configured to correlate coordinates of the region of the plurality of non-intersecting regions from the coordinate system of the localizer image to the coordinate system of the plurality of image slices to produce the image slice coordinate range by:

mapping a first boundary and a second boundary of the region from a first axis in the coordinate system of the localizer image, to a second axis in the coordinate system of the plurality of image slices, to produce the image slice coordinate range.

19. A system comprising:

a non-transitory memory, wherein the non-transitory memory stores instructions, and a trained machine learning model;

a display device; and a processor, wherein the processor is communicably coupled to the non-transitory memory and the display device, and wherein the processor, when executing the instructions, is configured to:

receive a localizer image of an imaging subject and a plurality of image slices corresponding to the localizer image;

map the localizer image to one or more bounding boxes using the trained machine learning model;

post-process the one or more bounding boxes to produce a coherent set of bounding boxes;

resolve boundaries of the coherent set of bounding boxes to produce a plurality of non-intersecting regions;

correlate coordinates of a region of the plurality of non-intersecting regions from a coordinate system of the localizer image to a coordinate system of the plurality of image slices to produce an image slice coordinate range;

label a subset of the plurality of image slices as belonging to the region of the imaging subject based on the image slice coordinate range; and displaying the subset of the plurality of image slices via the display device;

wherein the processor is configured to correlate coordinates of the region of the plurality of non-intersecting regions from the coordinate system of the localizer image to the coordinate system of the plurality of image slices to produce the image slice coordinate range by:

mapping a first boundary and a second boundary of the region from a first axis in the coordinate system of the localizer image, to a second axis in the coordinate system of the plurality of image slices, to produce the image slice coordinate range, wherein a mapping between the first axis and the second axis is given by:

$$Z_k = Z_{ref} + Y_k * \text{Spacing}_{\frac{Z}{Y}} * \cos \theta$$

where $Z_k$ is a distance of a point k along the second axis, $Z_{ref}$ is an offset between an origin of the first axis and an origin of the second axis, $Y_k$ is a distance of the point k along the first axis, $\text{Spacing}_{\frac{Z}{Y}}$ is a ratio between distance along the second axis and distance along the first axis, and $\theta$ is an angle between the first axis and the second axis.

20. The system of claim 13, wherein the processor is configured to label the subset of the plurality of image slices as belonging to one of a head region, a shoulder region, a chest region, an abdomen region, a pelvis region, and a legs region.

* * * * *